United States Patent [19]
Pegg et al.

[11] Patent Number: 5,955,463
[45] Date of Patent: Sep. 21, 1999

[54] QUINAZOLINE THYMIDYLATE SYNTHASE INHIBITORS

[75] Inventors: Stephen John Pegg; James Michael Wardleworth, both of Macclesfield, United Kingdom

[73] Assignees: Zeneca Limited; British Technology Group Ltd., both of London, United Kingdom

[21] Appl. No.: 08/028,158

[22] Filed: Mar. 9, 1993

[30] Foreign Application Priority Data

Mar. 11, 1992 [GB] United Kingdom .................. 9205320

[51] Int. Cl.$^6$ ....................... A61K 31/505; C07D 403/12
[52] U.S. Cl. .................................... 514/259; 544/284
[58] Field of Search ............................. 544/284; 514/259

[56] References Cited

U.S. PATENT DOCUMENTS

| | | | |
|---|---|---|---|
| 4,447,608 | 5/1984 | Jones et al. | 544/287 |
| 4,564,616 | 1/1986 | Jones et al. | 514/260 |
| 4,725,687 | 2/1988 | Pipe et al. | 544/279 |
| 4,857,530 | 8/1989 | Berman et al. | 514/259 |
| 4,981,856 | 1/1991 | Hughes | 514/259 |
| 4,992,550 | 2/1991 | Hughes | 544/284 |
| 4,999,424 | 3/1991 | BenRovic et al. | 536/22 |
| 5,081,124 | 1/1992 | Hughes | 514/259 |
| 5,089,499 | 2/1992 | Barker et al. | 514/259 |
| 5,145,854 | 9/1992 | Noir et al. | 514/259 |
| 5,187,167 | 2/1993 | Hughes | 514/259 |
| 5,252,573 | 10/1993 | Barker et al. | 514/259 |
| 5,280,027 | 1/1994 | Andrew et al. | 514/259 |

FOREIGN PATENT DOCUMENTS 2175903 12/1986 United Kingdom .

OTHER PUBLICATIONS

Varney et al. "Recent Advances In Antifolates As Anticancer Agents", Current Opinion In Therapeutic Patents Dec., 1992, No. 12, pp. 1979–1992.
Chemistry & Biology of Pteridines (1989) pp. 1154 to 1157 (Kalman et al.).
Cancer Research (1990),50, 1726–1731, McGuire et al.

*Primary Examiner*—Mathew Grumbling
*Attorney, Agent, or Firm*—Cushman Darby & Cushman, L.L.P.

[57] ABSTRACT

The invention relates to quinazoline derivatives or pharceutically-acceptable salts thereof, which possess anti-tumor activity; to processes for their manufacture; and to pharmaceutical compositions containing them.

The invention provides a quinazoline of the formula:

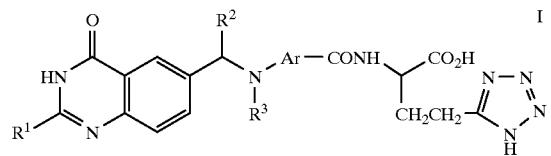

wherein $R^1$ is (1–4C)alkyl;

the quinazoline ring may optionally bear one or two further substituents selected from halogeno, (1–4C) alkyl and (1–4C)alkoxy;

$R^2$ is hydrogen or (1–4C)alkyl;

$R^3$ includes hydrogen and (1–4C)alkyl; and

Ar is optionally substituted phenylene or heterocyclene;

or a pharmaceutically-acceptable salt or ester thereof.

17 Claims, No Drawings

QUINAZOLINE THYMIDYLATE SYNTHASE INHIBITORS

This invention relates to novel anti-tumour compounds and more particularly it relates to quinazoline derivatives, or phamaceutically-acceptable salts or asters thereof, which possess anti-tumour activity. The invention includes novel quinazoline derivatives and processes for their manufacture; novel pharmaceutical compositions containing said quinazoline derivatives and the use of said quinazoline derivatives in the manufacture of novel medicaments for use in the production of an anti-tumour effect in a warm-blooded animal such as man.

One group of anti-tumour compounds comprises the antimetabolites, such as aminopterin and methotrexate, which are inhibitors of enzymes such as dihydrofolate reductase which act on folic acid derivatives. A newer compound which showed considerable promise in clinical trials is known as CB3717 and is described and claimed in United Kingdom Patent Specification No. 2065653B. Despite its promising activity against human breast, ovarian and liver cancer however, CB3717 shows symptoms of toxicity in humans, particularly in relation to the liver and kidney [Calvert, Alison, Harland, Robinson, Jackman, Jones, Newell, Siddik, Whiltshaw, McElwain, Smith and Harrap, *J. Clin. Oncol.*, 1986, 4, 1245; Cantwell, Earnshaw and Harris, *Cancer Treatment Reports*, 1986, 70, 1335; Barsendine, Curtin, Loose, Harris and James, *J. Hepatol.*, 1987, 4, 39; Vest, Bork and Hasen, *Eur. J. Cancer Clin. Oncol.*, 1988, 24, 201; Cantwell, Macaulay, Harris, Kaye, Smith, Milsted and Calvert, *Eur. J. Cancer Clin. Oncol.*, 1988, 24, 733; Sessa, Zucchetti, Ginier, Willems, D'Incalci and Cavalli, *Eur. J. Cancer Clin. Oncol.*, 1988, 24, 769]. Such adverse side effects are reduced in compounds in which the 2-amino substituent of CB3717 is either missing or is replaced by one of various alternative substituents as disclosed respectively in United Kingdom Patent Specification Nos. 2175903 and 2188319.

Compounds of the CB3717-type are believed to act as anti-cancer agents not by inhibition the enzyme dihydrofolate reductase but by inhibiting the enzyme thymidylate synthase. Thymidylate synthase catalyses the methylation of deoxyuridine monophosphate to produce thymidine monophosphate which is required for DNA synthesis. The anti-cancer activity of C3371 may be assessed in vitro by determining its inhibitory effect on that enzyme and in cell cultures by its inhibitory effect on cancer cell lines such as the mouse leukaemia cell line L1210, the mouse lymphoma cell lines L5178Y TK-/- and L5178Y TK+/- and the human breast cancer call line MCF-7.

Other compounds of the CB37L7-type may therefore have their anti-cancer activity assessed and compared with that of CB3717 by their activity against, for enaple, the same enzyme and the same cancer cell lines.

Antimetabolites, such as aminopterin and methotrexate, which are inhibitors of enzymes such as dihydrofolate reductase which act on folic acid derivatives, have also shown promise in the treatment of various allergic diseases such as allergic rhinitis, atopic dermatitis and psoriasis. The quinazoline derivatives of the present invention, being antimetabolites, are thus of value as therapeutic agents in the treatment of, for example, allergic conditions such as psoriasis.

Antimetabolites such as methotrexate have also shown promise in the treatment of various inflammatory diseases such as inflammation of the joints (especially rheumatoid arthritis, osteoarthritis and gout) and inflammation of the gastrointestinal tract (especially inflammatory bowel disease, ulcerative colitis and gastritis) [Weinblatt et al, *New England J. Med.*, 1985 312, 818; Andersen et al., *Ann. Internat. Med.*, 1985, 103, 489; Healey, *Bull. Rheum. Dis.*, 1986; 36, 1]. The quinazoline derivatives of the present invention are thus of value as therapeutic agents in the treatment of, for example, inflammatory disease such as rheumatoid arthritis.

European Patent Applications Nos. 0239362 and 0284338 disclose two series of quinazoline derivatives which possess anti-cancer properties by virtue of their inhibitory activity against thymidylate synthase. Many of the examples therein are N-{p-[N-(4-oxo-3,4-dihydroquinazolin-6-ylmethyl)-N-alkylamino]benzoyl}-L-glutamic acid derivatives. It is believed to be the case that these compounds, like the earlier compound CB3717, act through the metabolite produced on gamma-polyglutamylation. [Sikora et al., *Biochem. Pharmacol.*, 1988, 34, 4047; Jackman et al., *Cancer Research*, 1992, 51, 5579].

We have now surprisingly found that the structures of the known L-glutamic acid derivatives may be changed by the removal of the gamma-carboxy group and its replacement with a tetrazol-5-yl group to obtain compounds with improved inhibitory potencies against thymidylate synthase. In addition the compounds of the present invention are believed to act directly as the process of gamma-glutamylation cannot operate. This alternative mode of action of the compounds of the present invention provides the potential for more precise control of the anti-cancer effect since the onset of action should be more rapid as it is not dependent on a metabolic process which may vary in degree between patients. Moreover the compounds of the present invention are expected to be more useful in the treatment of cancers wherein the gamma-polyglutamation process is not operable than those earlier compounds which are believed to require gama-polyglutamylation to enhance their anti-cancer effect. Furthermore the process of polyglutamylation generally operates to produce polyglutamylated derivatives of antimetabolites which do not readily diffuse across cell membranes. In the event that a beneficial anti-cancer effect is outweighed by a detrimental toxic effects it is disadvantageous if the antimetabolite is retained in normal cells by virtue of the polyglutamylation process. The alternative mode of action of the compounds of the present invention thereby provides the potential for more precise control of the anti-cancer therapy provided to the patient.

According to the Invention there is provided a quinazoline derivative of the formula I (set out hereinafter) wherein $R^1$ is (1–4C)alkyl;

the quinazoline ring may optionally bear (at one or two of the 5-, 7- and 8-positions) one or two further substituents selected from halogeno, (1–4C)alkyl and (1–4C)alkoxy;

$R^2$ is hydrogen or (1–4C)alkyl;

$R^3$ is hydrogen, (1–4C)alkyl, (3–4C)alkenyl, (3–4C)alkynyl, hydroxy-(2–4C)alkyl, halogeno-(2–4C)alkyl or cyano-(1–4C)alkyl;

and Ar is phenylene or heterocyclene which may optionally bear one or two substituents selected from halogeno, (1–4C)alkyl and (1–4C)alkoxy; or a pharmaceutically-acceptable salt or ester thereof.

The chemical formulae referred to herein by Roman numerals are set out for convenience on separate sheets hereinafter. In this specification the term "alkyl" includes both straight and branched chain alkyl groups but references to individual alkyl groups such as "propyl" are specific for the straight chain version only. An analogous convention applies to other generic terms.

It will be observed that a quinazoline derivative of the invention possesses one or more asymmetric carbon atoms and it therefore exists in optically active forms. It is to be understood that this invention encompasses any optically-active form which possesses anti-tumour activity, it being a matter of common general knowledge how said optically-active forms may be separated. In its preferred form the quinazoline derivative of the invention is enriched in the form having the (S)-configuration at the carbon atom which bears the carboxy group i.e. the ratio of (S):(R) form is greater than 1:1. More preferably the quinazoline derivative of the invention has predominantly the (S)-configuration at said carbon atom i.e. the ratio of (S):(R) form is greater than 3:2. Yet more preferably the quinazoline derivative is substantially-free of the form having the (R)-configuration at said carbon atom. The term "substantially-free" is used herein to indicate the presence of no more than 10%, especially no more than 5% and most especially no more than 2% by weight of any such (R)-form.

Within the present invention it is to be understood that a quinazoline derivative of the formula I may exhibit the phenomenon of tautomerism. The formulae drawings presented within this specification can represent only one of the possible tautomeric forms. In particular it will be appreciated that the tetrazol-5-yl group may be in the form, for example, of a 1H-tetrazol-5-yl group or a 3H-tetrazol-5-yl group. It is to be understood that the invention encompasses any tautomeric form which possesses anti-tumour activity and is not to be limited merely to any one tautomeric form utilised within the formulae drawings.

It is also to be understood that certain quinazoline derivatives of the formula I can exist in solvated as well as unsolvated forms such as, for example, hydrated forms. It is to be understood that the invention encompasses all such solvated forms which possess anti-tumour activity.

Suitable values for the generic radicals referred to above include those set out below.

A suitable value for $R^1$, $R^2$ or $R^3$ when it is (1–4C)alkyl, or for a (1–4C)alkyl substituent which may be present on the quinazoline ring or on Ar is, for example, methyl, ethyl, propyl, isopropyl or butyl.

A suitable value for a (1–4C)alkoxy substituent which may be present on the quinazoline ring or on Ar is, for example, methoxy, ethoxy, propoxy, isopropoxy or butoxy.

A suitable value for a halogeno substituent which may be present on the quinazoline ring or on Ar is, for example, fluoro, chloro or bromo.

A suitable value for $R^3$ when it is (3–4C)alkenyl is, for example, prop-2-enyl, but-2-enyl, but-3-enyl or 2-methylprop-2-enyl; when it is (3–4C) alkynyl is, for example, prop-2-ynyl or but-3-ynyl; when it is hydroxy-(2–4C)alkyl is, for example, 2-hydroxyethyl or 3-hydroxypropyl; when it is halogeno-(2–4C)alkyl is, for example, 2-fluoroethyl, 2-chloroethyl, 2-bromoethyl, 3-fluoropropyl, 3-chloropropyl or 3-bromopropyl; and when it is cyano-(1–4C)alkyl is, for example, cyanomethyl, 2-cyanoethyl or 3-cyanopropyl.

A suitable value for Ar when it is phenylene is, for example 1,3- or 1,4-phenylene.

A suitable value for Ar when It is heterocyclene is, for example, a 5- or 6-membered aromatic (that is, fully unsaturated) heterocyclene ring which contains up to 3 heteroatoms selected from nitrogen and sulphur, for example, thiophenediyl, pyridinediyl, pyrimidinediyl or thiazolediyl. Conveniently Ar when it is heterocyclene is, for example, thiophene-2,4-diyl, thiophene-2,5-diyl, pyridine-2,5-diyl or thiazole-2,5-diyl.

A suitable pharmaceutically-acceptable salt of a quinazoline derivative of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmceutically-acceptable salt of a quinazoline derivative of the invention which is sufficiently acidic is an alkali metal salt, for example a sodium or potassium salt, an a alkaline earth metal salt, for example a calcium or magnesium salt, an ammonium or tetra-(2-hydroxyethyl)ammonium salt or a salt with an organic base which affords a physiologically-acceptable cation, for example a salt with methylamine, trimethylamine or tris-(2-hydroxyethyl)amine.

A suitable pharmaceutically-acceptable ester of a quinazoline derivative of the invention is, for example, an ester with a (1–6C)alcohol, for example a methyl, ethyl or tert-butyl ester.

Particular novel compounds of the invention are, for example, quinazoline derivatives of the formula I wherein:

(a) $R^1$ is a methyl or ethyl; and the quinazoline ring substituents, $R^2$, $R^3$ and Ar have any of the meanings defined hereinbefore or in this section defining particular novel compounds of the invention;

(b) the quinazoline ring bears at the 7-position one further substituent selected from fluoro, chloro, bromo and methyl; and $R^1$, $R^2$, $R^3$ and Ar have any of the meanings defined hereinbefore or in this section defining particular novel compounds of the invention;

(c) $R^2$ is hydrogen; and $R^1$, the quinazoline ring substituents, $R^3$ and Ar have any of the meanings defined hereinbefore or in this section defining particular novel compounds of the invention;

(d) $R^3$ is methyl, ethyl, propyl, prop-2-enyl9 prop-2-ynyl, 2-hydroxyethyl, 2-fluoroethyl, 2-bromoethyl or cyanomethyl; and $R^1$, the quinazoline ring substituents, $R^2$ and Ar have any of the meanings defined hereinbefore or in this section defining particular novel compounds of the invention; or (e) Ar is 1,4-phenylene which may optionally bear one or two substituents selected from fluoro, chloro, methyl and methoxy, or Ar is thiophene-2,5-diyl, thiazole-2,5-diyl or pyridine2,5-diyl; and $R^1$, the quinazoline ring substituents, $R^2$ and $R^3$ have any of the meanings defined hereinbefore or in this section defining particular novel compounds of the invention;

or a phamaceutically-acceptable salt or ester thereof.

A further particular compound of the invention comprises a quinazoline derivative of the formula I wherein $R^1$ is methyl;

the quinazoline ring may optionally bear a 7-fluoro, 7-chloro, 7-bromo or 7-methyl substituent;

$R^2$ is hydrogen;

$R^3$ is methyl, ethyl, propyl, prop-2-enyl or prop-2-ynyl; and

Ar is 1,4-phenylene which may optionally bear one fluoro substituent, or Ar is thiophene-2,5-diyl, thiazole-2,5-diyl (with the —CONH— group in the 2-position) or pyridine-2,5-diyl (with the —CONH— group in the 2-position);

or a pharmaceutically-acceptable salt thereof.

A further preferred compound of the Invention comprises a quinazoline derivative of the formula I wherein $R^1$ is methyl;

the quinazoline ring may optionally bear a 7-fluoro, 7-chloro, 7-bromo or 7-methyl substituent;

$R^2$ is hydrogen;

$R^3$ is methyl, ethyl or prop-2-ynyl; and

Ar is 1,4-phenylene-2-fluoro-1,4-phenylene (with the —CONH— group in the 1-position), or pyridine-2,5-diyl (with the —CONH— group in the 2-position);

or a pharmaceutically-acceptable salt thereof.

A further particular compound of the invention comprises a quinazoline derivative of the formula I wherein $R^1$ is methyl;

the quinazoline ring may optionally bear a 7-fluoro, 7-chloro, 7-bromo or 7-methyl substituent;

$R^2$ is hydrogen;

$R^3$ is methyl, ethyl, propyl, prop-2-enyl or prop-2-ynyl; and

Ar is 1,4-phenylene which may optionally bear one fluoro substituent, or Ar is thiophene-2,5-diyl or thiazole-2,5-diyl (with the —CONH— group in the 2-position);

or a pharmaceutically-acceptable salt thereof.

A specific preferred quinazoline derivative of the invention is, for example, one of the following quinazoline derivatives of the formula I, or a pharmaceutically-acceptable salt thereof:

2-{p-[N-(2-methyl-4-oxo-3,4-dihydroquinazolin-6-ylmethyl)-N-)prop-2-ynyl)amino]benzamido}-4-(tetrazol-5-yl)butyric acid, 2-{o-fluoro-p-[N-(2-methyl-4-oxo-3,4-dihydroquinazolin-6-ylmethyl)-N-(prop-2-ynyl)amino]benzamido}-4-(tetrazol-5 -yl)butyric acid, 2-{p-[N-(2,7-dimethyl-4-oxo-3,4-dihydroquinazolin-6-ylmethyl)-N-methylamino]benzamido}-4-(tetrazol-5-yl) butyric acid, 2-{o-fluoro-p-[N-(2,7-dimethyl-4-oxo-3,4-dihydroquinazolin-6-ylmethyl)-N-methylamino]benzamido}-4-(tetrazol-5-yl)butyric acid, 2-{p-[N-(2 7-dimethyl-4-oxo-3,4-dihydroquinazolin-6-ylmethyl)-N-(prop-2-ynyl)amino]benzamido}-4-(tetrazol-5-yl)butyric acid, 2-{o-fluoro-p-[N-(2,7-dimethyl-4-oxo-3,4-dihydroquinazolin-6-ylmethyl)-N-(prop-2-ynyl)amino]benzamido}-4-(tetrazol-5-yl)butyric acid, 2-{p-[N-(7-chloro-2-methyl-4-oxo-3,4-dihydroquinazolin-6-ylmethyl)-N-(prop-2-ynyl)amino]benzamido}-4-(tetrazol-5-yl)butyric acid, 2-{o-fluoro-p-[N-(7-chloro-2-methyl-4-oxo-3,4-dihydroquinazolin-6-ylmethyl)-N-(prop-2-ynyl)amino]benzamido}-4°(tetrazol-5-yl)butyric acid or 2-{p-[N-(7-bromo-2-methyl-4-oxo-3,4-dihydroquinazolin-6-ylmethyl)-N-(prop-2-ynyl)amino]benzamido}-4-(tetrazol-5-yl)butyric acid.

A further specific preferred quinazoline derivative of the invention is, for example, one of the following quinazoline derivatives of the formula I, or a pharmaceutically-acceptable salt thereof:

(2S)-2-{p-[N-(2-methyl-4-oxo-3,4-dihydroquinazolin-6-ylmethyl)-N-(prop-2-ynyl)amino]benzamido}-4-(tetrazol-5-yl)butyric acid, (2S)-2-{o-fluoro-p-[N-(2-methyl-4-oxo-3,4-dihydroquinazolin-6-ylmethyl)-N-(prop-2-ynyl)amino]benzamido}-4-(tetrazol-5-yl)butyric acid, (2S)-2-{p-[N-(2,7-dimethyl-4-oxo-3,4-dihydroquinazolin-6-ylmethyl)-N-methylamino]benzamido}-4-(tetrazol-5-yl)butyric acid, (2S)-2-{o-fluoro-p-[N-(2,7-dimethyl-4-oxo-3,4-dihydroquinazolin-6-ylmethyl)-N-methylamino]benzamido}-4-(tetrazol-5-yl)butyric acid, (2S)-2-{p-[N-(2,7-dimethyl-4oxo-3,4dihydroquinazolin-6-ylethyl)-N-(prop-2-ynyl)amino]benzamido}-4-(tetrazol-5-yl)butyric acid, (2S)-2-{o-fluoro-p-[N-(2,7-dimethyl-4-oxo-3,4-dihydroquinazolin-6-ylmethyl)-N-(prop-2-ynyl)amino]benzamido}-4-(tetrazol-5-yl)butyric acid, (2S)-2-{p-[N-(7-chloro-2-methyl-4-oxo-3,4-dihydroquinazolin-6-ylmethyl)-N-(prop-2-ynyl)amino]benzamido}-4-(tetrazol-5-yl)butyric acid, (2S)-2-{o-fluoro-p-[N-(7-chloro-2-methyl-4-oxo-3,4-dihydroquinazolin-6-ylmethyl)-N-(prop-2-ynyl)amino]benzamido}-4-(tetrazol-5-yl)butyric acid or (2S)-2-{p-[N-(7-bromo-2-methyl4-oxo-3,4-dihydroquinazolin-6-ylmethyl)-N-(prop-2-ynyl)amino]benzamido}-4-(tetrazol-5-yl)butyric acid.

Although such a quinazoline derivative of the (S)-configuration may occur in admixture with the corresponding derivative of the (R)-configuration, a preference for the presence of a greater amount of the derivative of the (S)-configuration has been indicated hereinbefore.

A further specific preferred quinazoline derivative of the invention is, for examples one of the following quinazoline derivatives of the formula I, 9 or a pharmaceutically-acceptable salt thereof:

(2S)-2-{o-fluoro-p-[N-(2,7-dimethyl-4-oxo-3,4-dihydroquinazolin-6-ylmethyl)-N-(prop-2-ynyl)amino]benzamido}-4-(tetrazol-5-yl)butyric acid or (2S)-2-{5-[N-(2,7-dimethyl-4-oxo-3,4-dihydroquinazolin-6-ylmethyl)-N-(prop-2-ynyl)amino]pyridine-2-carboxamido}-4-(tetrazol-5-yl)butyric acid.

In a further aspect of the present invention there is provided a group of quinazoline derivatives which possess improved anti-tumour activity and which in addition may possess improved therapeutic ratios compared to the activity and therapeutic ratios possessed by the structurally-closest known N-{p-[N-(4-oxo-3,4-dihydroquinazolin-6-ylmethyl))-N-alkylamino]benzoyl}-L-glutamic acid derivatives.

Conveniently this group of quinazoline derivatives comprises a quinazoline derivative of the formula I wherein $R^1$ is methyl;

the quinazoline ring bears a 7-methyl substituent;

$R^2$ is hydrogen;

$R^3$ is methyl, ethyl or prop-2-ynyl; and

Ar is 1,4-phenylene or 2-fluoro-1,4-phenylene (with the —CONH— group in the 1-position);

or a pharmaceutically-acceptable salt thereof.

Alternatively this group of quinazoline derivatives comprises a quinazoline derivative of the formula I wherein $R^1$ is methyl;

the quinazoline ring bears a 7-methyl substituent;

$R^2$ is hydrogen;

$R^3$ is methyl or prop-2-ynyl; and

Ar is 1,4-phenylene, 2-fluoro-1,4-phenylene (with the —CONH— group in the 1-position) or pyridine-2,5-diyl (with the —CONH— group in the 2-position);

or a pharmaceutically-acceptable salt thereof.

Preferably this group of quinazoline derivatives is represented by:

2-{o-fluoro-p-[N-(2,7-dimethyl-4-oxo-3,4-dihydroquinazolin-6-ylmethyl)-N-methylamino]benzamido}-4-(tetrazol-5-yl)butyric acid; or a pharmaceutically-acceptable salt thereof.

Alternatively this group of quinazoline derivatives is represented by:

(2S)-2-{o-fluoro-p-[N-(2,7-dimethyl-4-oxo-3,4-dihydroquinazolin-6-ylmethyl)-N-(prop-2-ynyl)amino]benzamido-4-(tetrazol-5-yl)butyric acid; or a pharmaceutically-acceptable salt thereof.

Alternatively this group of quinazoline derivatives is represented by:

(2S)-2-{5-[N-(2,7-dimethyl-4-oxo-3,4-dihydroquinazolin-6-ylmethyl)-N-(prop-2-ynyl)amino]pyridine-2-carboxamido}-4-(tetrazol-5-yl)butyric acid; or a pharmaceutically-acceptable salt thereof.

The therapeutic ratio of a quinazoline derivative of the invention may be determined, for example, by comparing the dose which gives effective anti-tumour activity in a suitable in vivo model such as a L5178Y TK +/− tumour [Fischer et al., *Methods in medical Research*, 1964, 10, 247] in a suitable animal species such as the mouse, with the dose which gives significant weight loss in the test animal species.

A compound of the Invention comprising a quinazoline derivative of the formula I, or a phamaceutically-acceptable salt or ester thereof, may be prepared by any process known to be applicable to the preparation of structurally-related compounds. Such procedures are provided as a further feature of the invention and are illustrated by the following representative examples in which, unless otherwise stated, $R^1$, $R^2$, $R^3$ and Ar have any of the meanings defined hereinbefore. Alternatively, where appropriate, conventional protecting groups are utilised on functional groups which would otherwise interfere with the required process. Examples of such conventional protecting groups are provided hereinafter. Any such protecting groups are, where desired, removed by conventional means.

(a) The reaction of an acid of the formula II (set out hereinafter), or a reactive derivative thereof, wherein $R^4$ is hydrogen or a protecting group, with a compound of the formula III, whereln $R^5$ is a protecting group such as a (1–4C)alkyl group, whereafter the protecting groups are removed by conventional means.

A suitable reactive derivative of an acid of the formula II may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol or an alcohol such as 1-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxides potassium hydroxides sodium hydride or potassium hydride, or, for example, an organic amine base such as, for examples pyridine, 2,6-lutidine collidine, 4-dimethylaminopyridine, triethylamine, morpholine or diazabicyclo[5.4.0]undec-7-ene. The reaction is also preferably carried out in a suitable inert solvent or diluent, for example tetrahydrofuran, 1,2-dimethoxyethane, N,N-dimethylformamide, N,N,-dimethylacetamide, N-methylpyrrolidin-2-one, dimethylsulphoxide or acetone, and at a temperature in the range, for example, −78° to 150° C., conveniently at or near ambient temperature.

A suitable value for $R^4$ when it is a protecting group is, for example, a pivaloyloxymethyl group which may be removed by hydrolysis with a base, for example sodium hydroxide or ammonia; in a suitable inert solvent or diluent; for example methanol or ethanol.

A suitable value for $R^5$ when it is a (1–4C)alkyl group is, for example, a methyl, ethyl, propyl, isopropyl, butyl, isobutyl or tert-butyl group. $R^5$ may be removed, for example, by hydrolysis conveniently in the presence of a suitable base such as, for example, an alkali or alkaline earth metal hydroxide, for example lithium hydroxide, sodium hydroxide or potassium hydroxide. Alternatively, when $R^5$ is, for example, a tert-butyl group it may be removed, for example, by treatment with a suitable inorganic acid such as hydrochloric, sulphuric or phosphoric acid or with a suitable organic acid such as trifluoroacetic acid.

A suitable protecting group for a hydroxy-(2–4C)alkyl group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula II and of the formula III may be prepared by standard procedures of organic chemistry. The preparation of examples of such starting materials is described within the accompanying non-limiting Examples which are provided for the purpose of illustration only. Other necessary starting materials are obtainable by analogous procedures to those described or by modifications thereto which are within the ordinary skill of an organic chemist. Thus, for example, the starting material of the formula II may be prepared by the reaction of a compound of the formula IV wherein Z is a displaceable group, with an amine of the formula:

wherein $R^5$ is a protecting group as defined hereinbefore which can be removed to provide a carboxylic acid. In addition, for example, the starting material of the formula III wherein $R^5$ is hydrogen and having predominantly the (S)-configuration at the carbon atom which carries the amino and carboxy groups is known (*Tetrahedron*, 1977, 33, 2299). This may be esterified by conventional means to form a compound of the formula III wherein $R^5$ is a (1–4C)alkyl group. Alternatively the compound disclosed therein, which has the structure of the compound of the formula III wherein $R^5$ is methyl except that the amino group is protected by a benzyloxycarbonyl group, may be deprotected, for example by hydrogenolysis.

A suitable value for the displaceable group Z is, for example, a halogeno or sulphonyloxy group, for example a chloro, bromo, methylsulphonyloxy or 4-toluenesulphonyloxy group.

(b) The reaction of a compound of the formula IV wherein $R^4$ is hydrogen or a protecting group as defined hereinbefore and Z is a displaceable group as defined hereinbefore, with an amine of the formula V wherein $R^5$ is a protecting group as defined hereinbefore, whereafter the protecting groups are removed by conventional means.

The reaction is preferably carried out in the presence of a suitable base as defined above, in a suitable inert solvent or diluent as defined above, and at a temperature in the range, for example 25° to 150° C., conveniently at or near 90° C.

The starting materials of the formula IV and of the formula V may be prepared by standard procedures of organic chemistry. The preparation of examples of compounds of the formula IV is described by way of reference within the accompanying non-limiting Examples which are provided for the purpose of illustration only. Other necessary starting materials are obtainable by analogous procedures to those described or by modifications thereto which are within the ordinary skill of an organic chemist.

When a pharmaceutically-acceptable salt of a novel compound of the formula I is required, it may be obtained, for examples by reaction of said compound with a suitable acid or base using a conventional procedure. When a pharmaceutically-acceptable ester of a novel compound of the formula I is required, it may be obtained, for example, by reaction of said compound with a suitable (1–6C)alcohol using a conventional procedure. When an optically active form of a compound of the formula I is required, it may be obtained by carrying out one of the aforesaid processes using an optically active starting material, or by resolution of a racemic form of said compound using a conventional procedure.

As stated above a quinazoline derivative of the present invention possesses anti-tumour activity. This activity may be assessed, for example, using one or more of the procedures set out below.

(a) An in vitro assay which determines the ability of a test compound to inhibit the enzyme thymidylate synthase. Thymidylate synthase was obtained in partially purified form from L1210 mouse leukaemia cells and utilised using the procedures described by Jackman et al. (*Cancer Res.*, 1986, 46, 2810 and Sikora et al., *Biochem. Pharmacol.* 1988, 37, 4047).

(b) An assay which determines the ability of a test compound to inhibit the growth of the leukaemia cell line L1210 in cell culture. The test is similar to that described in UK Patent Specification No. 2065653B and has been described by Jones et al., *J. Med. Chem.*, 1985, 28, 1468.

(c) An assay which determines the ability of a test compound to inhibit the growth of the human breast cancer cell line MCF-7 in cell culture. The test is similar to that described by Lippman et al. (*Cancer Res.*, 1976 36; 4595).

Although the pharmacological properties of the quinazolines of the invention vary with structural changes, in general quinazolines of the invention possess activity in one or more of the above tests (a) to (c) as follows:

Test (a) $IC_{50}$ in the range, for example, 1–100 nM;

Test (b) $IC_{50}$ in the range, for example, 0.01–10 $\mu$H;

Test (c) $IC_{50}$ in the range, for example, 0.01–10 $\mu$M.

In general those quinazolines of the invention which are especially preferred possess activity in one or more of the above tests (a) to (c):

Test (a) $IC_{50}$ in the range, for example, 1–20 nM;

Test (b) $IC_{50}$ in the range, for example, 0.01–1 $\mu$M;

Test (c) $IC_{50}$ in the range, for example, 0.01–1 $\mu$M.

Thus by way of example, the compound:

(2S)-2-{p-[N-(2-methyl-4-oxo-3,4-dihydroquinazolin-6-ylmethyl)-N-(prop-2-ynyl)amino]benzamido}-4-(tetrazol-5-yl)butyric acid has an $IC_{50}$ of ~13 nM in Test (a), an $IC_{50}$ of ~0.12 $\mu$M in Test (b); and an $IC_{50}$ of ~0.04 $\mu$M in Test (c);

(2S)-2-{o-fluoro-p-[N-(2,7-dimethyl-4-oxo-3,4-dihydroquinazolin-6-ylmethyl)-N-methylamino]benzamido}-4-(tetrazol-5-yl)butyric acid has an $IC_{50}$ of ~2 nM in Test (a), an $IC_{50}$ ~0.07 $\mu$M in Test (b); and an $IC_{50}$ ~0.04 $\mu$M in Test (c); and (2S)-2-{o-fluoro-p-[N-(2,7-dimethyl-4-oxo-3,4-dihydroquinazolin-6-ylmethyl)-N-(prop-2-ynyl)amino]benzamido}-4-(tetrazol-5-yl)butyric acid has an $IC_{50}$ of ~1 nM in Test (a), an $IC_{50}$ of ~0.02 $\mu$M in Test (b), and an $IC_{50}$ of ~0.01 $\mu$M in Test (c).

A quinazoline derivative of the invention, or a pharmaceutically-acceptable salt or aster thereof, may be administered to a warm-blooded animal, including a human, in the form of a pharmaceutical composition which comprises the quinazoline derivative, or a pharmaceutically-acceptable salt or ester thereof, in association with a pharmaceutically-acceptable diluent or carrier.

The composition may be in a form suitable for oral use, for example a tablet, capsule, aqueous or oily solution, suspension or emulsion; for topical uses for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or especially for parenteral use (including intravenous, subcutaneous, intramuscular, intravascular or infusion), for example as a sterile aqueous or oily solution, emulsion or suspension. In general the above compositions may be prepared in a conventional manner using conventional excipients.

The composition may contain, in addition to the quinazoline derivative of the invention, one or more other anti-tumour substances, for example those selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide; and biological response modifiers, for example interferon.

The quinazoline will normally be administered to a warm-blooded animal at a unit dose within the range 50–5000 mg per square metre body area of the animal, i.e. approximately 1–100 mg/kg, and this normally provides a therapeutically-effective dose. A unit dose form such as a tablet or capsule will usually contain, for example, 1–250 mg of active ingredient. Preferably a daily dose in the range of 1–50 mg/kg preferably 1–15 mg/kg, is employed. However the daily dose will necessarily be varied depending upon the host treated, the particular route of administration, and the severity of the illness being treated. Accordingly the optimum dosage will be determined by the practitioner who is treating any particular patient.

According to a further feature of the invention there is provided a quinazoline derivative of the formula I, or a pharmaceutically-acceptable salt or ester thereof, for use in a method of treatment of the human or animal body by therapy.

According to a further feature of the present invention there is provided a method for producing an anti-tumour effect in a warm-blooded animal, such as man, in need of such treatment which comprises administering to said animal an effective amount of a quinazoline derivative of the present invention, or a pharmaceutically-acceptable salt or ester thereof.

The invention also provides the use of a quinazoline derivative of the present invention, or a pharmaceutically-acceptable salt or ester thereof, in the manufacture of a novel medicament for use in the production of an anti-tumour effect in a warm blooded animal, such as man.

A quinazoline of the present invention is expected to possess a wide range of anti-tumour activities. CB3717 showed promising activity against human breast, ovarian and liver cancer and consequently it is expected that a quinazoline of the present invention will possess anti-tumour activity against these cancers. It is in addition expected that a quinazoline of the present invention will possess anti-tumour activity against a range of leukaemias, lymphoid malignancies and solid tumours such as carcinomas and sarcomas. Such tumours require thymidine monophosphate as one of the essential nucleotides for the synthesis of cellular DNA. In the presence of an effective amount of a thymidylate synthase inhibitor such as an effective amount of a quinazoline derivative of the present invention it is expected that tumour growth will be inhibited.

As previously mentioned a quinazoline derivative of the invention, or a pharmaceutically-acceptable salt or ester thereof, is also of value in the treatment of, for example, allergic conditions such as psoriasis or inflammatory disease such as rheumatoid arthritis. In using a quinazoline of the invention for this purpose the compound will normally be administered at a dose within the range 500–50000 mg per square metre body area of the animal. In general for the treatment of an allergic condition such as psoriasis topical administration of a quinazoline of the Invention is preferred. Thus, for example, for topical administration a daily dose in the range, for example, 1 to 150 mg/kg, preferably 1 to 80 mg/kg, will be used.

The invention is illustrated but not limited by the following Examples in which unless otherwise stated:

(i) evaporations were carried out by rotary evaporation in vacuo and work-up procedures were carried out after removal of residual solids by filtration;

(ii) operations were carried out at laboratory temperature, that is in the range 18–20° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 reverse-phase silica (Art. 9303) obtained from E. Merck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques [proton magnetic resonance spectra were determined using a Jeol FX 90Q or a Bruker AM200 spectrometer operating at a field strength of 200 MHz; chemical shifts are reported in parts per million downfield from tetramethylsilane as an internal standard (δ scale) and peak multiplicities are shown thus: s, singlet; d, doublet; d of d's, doublet of doublet's; t, triplet, m, multiplet; fast-atom bombardment (FAB) mass spectral data were obtained using a VG Analytical MS9 spectrometer and xenon gas and, where appropriate, either positive ion data or negative ion data were collected];

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus, a Koffler hot plate appartus or an oil-bath apparatus;

(viii) the chiral purity of the end-products of the formula I and of intermediates such as those of the formula III was assessed using NMR and chromatographic analysis;

(ix) the following abbreviations have been used:
THF tetrahyrdrofuran;
N,N-dimethylformamide;
DMA N,N-methylacetamide;
NMP N-methylpyrrolidin-2-one;
DMSO dimethylsulphoxide.

EXAMPLE 1

A mixture of pentafluorophenyl o-fluoro-p-[N-(2,7-dimethyl-4-oxo-3-(pivaloyloxmethyl)-3,4-dihydroquinazolin-6-ylmethyl)-N-(prop-2-ynyl)amino]benzoate (2.5 g), methyl (2S)-2-amino-4-(tetrazol-5-yl)-butyrate (0.32 g), N-hydroxybenzotriasole (0.05 g) and DMF (100 ml) was stirred at ambient temperature for 24 hours. The mixture was evaporated and the residue was purified by column chromatography using a 19:1 v/v mixture of methylene chloride and methanol as eluent. There was thus obtained, as a gum which on trituration under diethyl ether-gave a solid (1.92 g), methyl (2S)-2-{o-fluoro-p-[N-(2,7-dimethyl-4-oxo-3-(pivaloyloxymethyl)-3,4-dihydroquinazolin-6-ylmethyl)-N-(prop-2-ynyl)amino]benzamido}-4-(tetrazol-5-yl)butyrate in 79% yield.

A mixture of the product so obtained, 2N sodium hydroxide solution (20 ml) and methanol (5 ml) was stirred at ambient temperature for 1 hour. The mixture was concentrated by evaporation of the methanol and the aqueous residue was acidified to pH4 by the addition of concentrated hydrochloric acid. The precipitate was isolated, washed with water and dried. There gas thus obtained (2S)-2-{o-fluoro-p-[N-(2,7-dimethyl-4-oxo-3,4-dihydroquinazolin-6-ylmethyl)-N-(prop-2-ynyl)amino]benzamido}-4-(tetrazol-5-yl)butyric acid (1.21 g, 79%), m.p. 232–240° C.

NMR Spectrum: ($CD_3SOCD_3$) 2.12–2.21 (m, 2H), 2.24 (s, 3H), 2.30 (s, 3H), 2.94 (m, 2H), 3.20 (s, 1H), 4.28 (s, 2H), 4.41 (m, 1H), 4.68 (s, 2H), 6.62 (m, 2H), 7.42 (s, 1H), 7.56 (t, 1H), 7.67 (s, 1H), 8.05 (t, 1H), 12.03 (s, 1H); Mass Spectrum: (positive ion FAB) m/e (P+1) 533; Elemental Analysis: Found C, 53.1; H, 4.4; H, 19.5; $C_{26}H_{25}FN_8O_4$ 0.99NaCl requires C, 53.4; H, 4.3; N, 19.2%.

In this example the methyl (2S)-2-amino-4-(tetrazol-5-yl)-butyrate was enriched in the form having the (S)-configuration at the carbon atom which bears the methoxycarbonyl group to the extent that the ratio of (S):(R) form was 7:3 as determined by chromatographic analysis. This isomeric ratio was retained in the product of Example 1.

The pentafluorophenyl o-fluoro-p-[N-(2,7-dimethyl-4-oxo-3-(pivaloyloxyethyl)-3,4-dihydroquinazolin-6-ylmethyl)-N-(prop-2-ynyl)-amino]benzoate used as a starting material was obtained as follows:

A mixture of tert-butyl o-fluoro-p-(prop-2-ynyl)amino-benzoate [0.882 g; prepared in 56% yield by the reaction of tert-butyl p-amino-o-fluorobenzoate (European Patent Application No. 0373891, Example 3 thereof) with propargyl bromide], 6-bromomethyl-2,7-dimethyl-3-(pivaloyloxymethyl)-3,4-dihydroquinazolin-4-one [0.9 g; European Patent Application No. 0459730, Example 13 thereof], potassium carbonate (0.691 g), 18-croun-6 (0.005 g) and NMP (20 ml) was stirred and heated to 90° C. for 6 hours. The mixture was evaporated and the residue was partitioned between ethyl acetate and water. The organic phase was washed with water and with brine, dried (MgSO$_4$) and evaporated. The residue was purified by column chromatography using increasingly polar mixtures of methylene chloride and ethyl acetate as eluent. There was thus obtained tert-butyl o-fluoro-p-[N-(2,7-dimethyl-4-oxo-3-(pivaloyloxymethyl)-3,4-dihydroquinazolin-6-ylmethyl)-N-(prop-2-ynyl)amino]benzoate (0.9 g).

A mixture of the product so obtained and trifluoroacetic acid (20 ml) was stirred at ambient temperature for 1 hour. The mixture was evaporated and the residue was triturated under diethyl ether. There was thus obtained o-fluoro-p-[N-(2,7-dimethyl-4-oxo-3-(pivaloyloxymethyl)-3,4-dihydroquinazolin-6-ylmethyl-N-(prop-2-ynyl)amino] benzoic acid as a solid (0.64 g).

Elemental Analysis: Found C, 64.7; H, 5.5; N, 8.2; $C_{27}H_{28}FN_3O_5$ 0.1$CF_3CO_2H$ requires C, 64.7; H, 5.6; N, 8.3%.

Dicyclohexylcarbodiimide (14.9 g) was added to a suspension of o-fluoro-p-[N-(2,7-dimethyl-4-oxo-3-(pivaloyloxymethyl)-3,4-dihydroquinazolin-6-ylmethyl)-N-(prop-2-ynyl)amino]benzoic acid (23.8 g) and pentafluorophenol (26.6 g) in DMF (200 ml) and the mixture was stirred at ambient temperature for 18 hours. The mixture was filtered and the filtrate was evaporated. The residue was purified by column chromatography using a 1:1 v/v mixture of hexane and ethyl acetate as eluent. There was thus obtained the required starting material (11 g), m.p. 163–165° C.

The methyl (2S)-2-amino-4-(tetrazol-5-yl)butyrate (in which the ratio of (S):(R) form was 7:3) used as a starting material was obtained as follows:

Sulphuryl chloride (1 g) was added to a stirred mixture of N-benzyloxycarbonyl-L-glutamine (100 g) and methanol (1200 ml) and the mixture was stirred at ambient temperature for 24 hours. The mixture was evaporated to give N-benzyloxycarbonyl-L-glutamine methyl ester (105 g).

p-Tosyl chloride (83.8 g) was added portionwise to a stirred mixture of the product so obtained and pyridine (200 ml) at such a rate that the temperature of the reaction mixture did not exceed 35° C. The mixture was then heated to 65° C. for 90 minutes. The mixture was concentrated by the evaporation of the pyridine and the residue was partitioned between ethyl acetate and waters The organic phase was washed with 2N aqueous hydrochloric acid and with water, dried (MgSO$_4$) and evaporated. The residue was purified by column chromatography using a 1:1 v/v mixture of hexane and ethyl acetate as eluent. There was thus obtained methyl (2S)-2-benzyloxycarbonylamino-4-cyanobutyrate (81 g).

A mixture of the product so obtained, sodium azide (22.2 g), ammonium chloride (18.3 g) and DMF (400 ml) was heated on a steam bath for 24 hours. The mixture was concentrated and water (55 ml) was added to the residue. The mixture was acidified to pH1 by the addition of concentrated hydrochloric acid and extracted with ethyl acetate. The organic extract was dried (MgSO$_4$) and evaporated. The residue was triturated under diethyl ether to give methyl (2S)-2-benzyloxycarbonylamino-4-(tetrazol-5-yl)butyrate (36 g; in which the ratio of (S):(R) form was 7:3).

NMR Spectrum: (CD$_3$SOCD$_3$) 1.95–2.35 (m, 2H), 2.95 (t, 2H), 3.64 (s, 3H), 4.15 (m, 1H), 5.04 (s, 2H), 7.36 (s, 5H), 7.88 (d, 1H), 13.0 (s, 1H).

A mixture of a portion (17.1 g) of the product so obtained, 10% palladium-on-charcoal catalyst (2.2 g) and ethanol (300 ml) was stirred at ambient temperature under an atmosphere of hydrogen for 24 hours. The mixture was filtered and the filtrate was evaporated. The residue was triturated under diethyl ether. There was thus obtained methyl (2S)-2-amino-4-(tetrazol-5-yl)butyrate (1.75; in which the ratio of (S):(R) for was 7:3), mp. 177–182° C.

EXAMPLE 2

The procedure described in Example 1 was repeated except that the appropriate pentafluorophenyl benzoate was reacted with (2S)-2-amino-4-(tetrazol-5-yl)butyrate. There were thus obtained the compounds described In the following Table, the structures of which were confirmed by proton magnetic resonance and mass spectroscopy and by elemental analysis. Unless otherwise stated, a batch of methyl (2S)-2-amino-4-(tetrazol-5-yl)butyrate was employed which was enriched in the form having the (S)-configuration to the extent that the ratio of the (S):(R) form was 7:3.

TABLE I

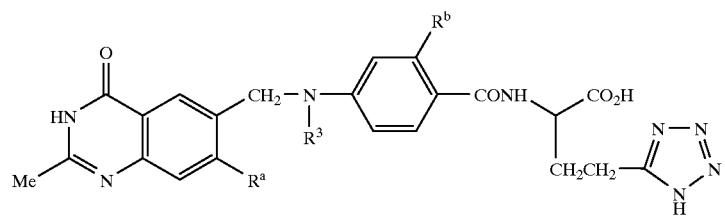

| Example 2 Compound No. | R$^3$ | R$^a$ | R$^b$ | m.p. (° C.) |
|---|---|---|---|---|
| 1$^a$ | prop-2-ynyl | H | H | 203–209 |
| 2$^b$ | prop-2-ynyl | H | F | 232–235 |
| 3$^c$ | methyl | H | H | oil |
| 4$^d$ | methyl | H | F | oil |
| 5$^e$ | methyl | methyl | H | 235–250 |
| 6$^f$ | methyl | methyl | F | 244–250 |
| 7$^g$ | prop-2-ynyl | methyl | H | 213–222 |
| 8$^h$ | prop-2-ynyl | F | H | oil |
| 9$^i$ | methyl | Cl | H | oil |
| 10$^j$ | prop-2-ynyl | Cl | H | 205–208 |
| 11$^k$ | prop-2-ynyl | Cl | F | 206 (decomposes) |

TABLE I-continued

| Example 2 Compound No. | R³ | Rᵃ | Rᵇ | m.p. (° C.) |
|---|---|---|---|---|
| 12[l] | methyl | Br | F | 233 (decomposes) |
| 13[m] | prop-2-ynyl | Br | H | >306 (decomposes) |
| 14[n] | prop-2-ynyl | Br | F | 217 (decomposes) |

Notes a) Elemental analysis showed that the product contained 1 equivalent of water and 0.5 equivalents of sodium chloride.

The pentafluorophenyl p-[N-(2-methyl-4-oxo-3-(pivaloyloxymethyl)-3,4-dihydroquinazolin-6-ylmethyl)-N-(prop-2-ynyl)amino]benzoate, used as a starting material, was obtained by the reaction of p-[N-9(2-methyl-4-oxo-3-(pivaloyloxymethyl)-3,4-dihydroquinazolin-6-ylmethyl)-N-(prop-2-ynyl)amino]benzoic acid (European Patent Application No. 0459730, Example 1 thereof) and pentafluorophenol using an analogous procedure to that described in the portion of Example 1 which is concerned with the preparation of starting materials.

The methyl (2S)-2-amino-4-(tetrazol-5-yl)butyrate utilised in the preparation of this product was obtained in a form substantially-free of the (R)-form utilising the procedure of Tran et al., *Tetrahedron*, 1977, 33, 2299.

b) Elemental analysis showed that the product contained 0.5 equivalents of water and 005 equivalents of sodium chloride.

The pentafluorophenyl o-fluoro-p-[N-(2-methyl-4-oxo-3-(pivaloyloxymethyl)-3,4-dihydroquinazolin-6-ylmethyl)-2-(prop-2-ynyl)-amino]benzoate, used as a starting material, was obtained by the reaction of o-fluoro-p-[N-(2-methyl-4-oxo-3-(pivaloyloxymethyl)-3,4-dihydroquinazolin-6-ylmethyl)-N-(prop-2-ynyl)amino]benzoic acid (European Patent Application No. 04597309 Example 13 thereof) and pentafluorophenol using an analogous procedure to that described in the portion of Example 1 which is concerned with the preparation of starting materials.

c) The product gave the following characteristic NMR signals: (CD₃SOCD₃) 2.21 (g 2H), 2.33 (s, 3H), 2.96 (t, 2H), 3.13 (s, 3H), 4.4 (m, 1H), 4.78 (s, 2H), 6.78 (d, 2H), 7.5–7.65 (m, 2H), 7.74 (d, 2H), 7.85 (d, 1H), 8.3 (d, 1H).

The pentafluorophenyl p-[N-(2-methyl-4-oxo-3-(pivaloyloxymethyl)-3,4-dihydroquinazolin-6-ylmethyl)-N-methylamino]benzoate, used as a starting material, was obtained from 6-bromomethyl-2-methyl-3-(pivaloyloxymethyl)-3,4-dihydroquinazolin-4-one [European Patent Application No. 02393629 Example 1 thereof] and tert-butyl p-methylaminobenzoate [prepared by the reaction of tert-butyl p-aminobenzoate with methyl iodide] using analogous procedures to those described in the portion of Example 1 which is concerned with the preparation of starting materials.

d) The product gave the following characteristic NMR signals: (CD₃SOCD₃) 2.0–2.25 (m, 2H), 2.3 (s, 3H), 2.9–3.0 (t, 2H), 3.1 (s, 3H), 4.35–4.5 (m, 1H), 4.8 (s, 2H), 6.7 (m, 2H), 7.57 (m, 3H), 7.9 (m, 2H), 12.08 (s, 1H).

The pentafluorophenyl o-fluoro-p-[N-(2-methyl-4-oxo-3-(pivaloyloxymethyl)-3,4-dihydroquinazolin-6-ylmethyl)-N-methylamino]benzoate, used as a starting material, was obtained from 6-bromomethyl-2-methyl-3-(pivaloyloxymethyl)-3,4-dihydroquinazolin-4-one and tert-butyl o-fluoro-p-methylaminobenzoate [prepared by the reaction of tert-butyl p-amino-o-fluorobenzoate with methyl iodide] using analogous procedures to those described in the portion of Example 1 which is concerned with the preparation of starting materials.

The methyl (2S)-2-amino-4-(tetrazol-5-yl)butyrate utilised in the preparation of this product was obtained in a form substantially-free of the (R)-form utilising the procedure of Tran et al., *Tetrahedron*, 1977, 33, 2299.

e) Elemental analysis showed that the product contained 1.2 equivalents of water.

The pentafluorophenyl p-[N-(2,7-dimethyl-4-oxo-3-(pivaloyloxymethyl)-3,4-dihydroquinazolin-6-ylmethyl)-N-methylamino]-benzoate, used as a starting material, was obtained from 6-bromomethyl-2,7-dimethyl-3-(pivaloyloxymethyl)-3,4-dihydroquinazolin-4-one and tert-butyl p-methylaminobenzoate using analogous procedures to those described in the portion of Example 1 which is concerned with the preparation of starting materials.

f) Elemental analysis showed that the product contained 0.5 equivalents of water and 0.45 equivalents of sodium chloride.

The pentafluorophenyl o-fluoro-p-[N-(2,7-dimethyl-4-oxo-3-(pivaloyloxymethyl)-3,4-dihydroquinazolin-6-methyl)-N-methylamino]benzoate, used as a starting material, was obtained from 6-bromomethyl-2,7-dimethyl-3-(pivaloyloxymethyl)-3,4 dihydroquinazolin-4-one and tert-butyl o-fluoro-p-methylaminobenzoate using analogous procedures to those described in the portion of Example 1 which is concerned with the preparation of starting materials.

g) Elemental analysis showed that the product contained 1 equivalent of water.

The pentafluorophenyl p-[N-2,7-dimethyl-4-oxo-3-(pivaloyloxymethyl)-3,4-dihydroquinazolin-6-ylmethyl)-N-(prop-2-ynyl)amino]benzoate, used as a starting material, was obtained by the reaction of p-[N-(2,7-dimethyl-4-oxo-3-(pivaloyloxymethyl)-3,4-dihydroquinazolin-6-ylmethyl)-N-(prop-2-ynyl)amino]benzoic acid (European Patent Application No. 0459730, Example 13 thereof) and pentafluorophenol using an analogous procedure to that described in the portion of Example 1 which is concerned with the preparation of starting materials.

h) The product gave the following characteristic NMR signals: (CD₃SOCD₃) 2.2 (m, 2H), 2.33 (sp 3H), 2.95 (t, 2H), 3.15 (s, 1H), 4.28–4.45 (m, 3H), 4.78 (s, 2H), 6.86(d, 2H), 7.35(d, 1H), 7.77 (d, 2H), 7.92 (d, 1H), 8.47 (m, 1H).

The pentafluorophenyl p-[N-(7-fluoro-2-methyl-4-oxo-3-(pivaloyloxymethyl)-3,4-dihydroquinazolin-6-ylmethyl)-N-(prop-2-ynyl)-amino]benzoate, used as a starting material, was obtained by the reaction of p-[N-(7-fluoro-2-methyl-4-oxo-3-(pivaloyloxymethyl)-3,4-dihydroquinazolin-6-ylmethyl)-N-(prop-2-ynyl)amino]benzoic acid (European Patent Application No. 0373891, Example 26 thereof) and pentafluorophenol using an analogous procedure to that described in the portion of Example 1 which is concerned with the preparation of starting materials.

i) The product gave the following characteristic NMR signals: (CD₃SOCD₃) 2.2 (m, 2H), 2.32 (s, 3H), 2.95 (t, 2H), 3.18 (s, 3H), 4.4. (m, 1H), 4.76 (s, 2H), 6.72 (d, 2H), 7.72 (q, 4H), 8.36 (d, 1H).

The pentafluorophenyl p-[N-(7-chloro-2-methyl-4-oxo-3-(pivaloyloxymethyl)-3,4-dihydroquinazolin-6-ylmethyl)-N-methylamino]-benzoate, used as a starting material, was obtained from 6-bromomethyl-7-chloro-2-methyl-3-(pivaloyloxymethyl)-3,4-dihydroquinazolin-4-one and tert-butyl 2-methylaminobenzoate using analogous procedures to those described in the portion of Example 1 which is concerned with the preparation of starting materials.

The 6-bromomethyl-7-chloro-2-methyl-3-(pivaloyloxymethyl)-3,4-dihydroquinazolin-4-one used immediately above was prepared from 7-chloro-2,6-dimethyl-3,4-dihydroquinazolin-4-one (European Patent Application No. 0284388, Example 2 thereof) using the following procedures:

7-Chloro-2,6-dimethyl-3,4-dihydroquinazolin-4-one (17 g) was added portionwise to a stirred suspension of sodium hydride (60% w/w dispersion in mineral oil, 2.9 g; washed with hexane to remove the mineral oil) in DMSO (200 ml) which was cooled to 20° C. The mixture was stirred at ambient temperature for 1 hour. Chloromethyl pivalate (23.7 ml) was added portionwise and the mixture was stirred at ambient temperature for 15 hours. The mixture was poured into water (150 ml) and extracted with ethyl acetate (3×70 ml). The combined extracts were washed with water, dried (MgSO₄) and evaporated The residue was triturated under diethyl ether to give 7-chloro-2,6-dimethyl-3-(pivaloyloxymethyl)-3,4-dihydroquinazolin-4-one as a solid (17 g).

A mixture of the product so obtained, N-bromosuccinimide (9.8 g), benzoyl peroxide (0.1 g) and carbon tetrachloride (400 ml) was heated to reflux for 4 hours. The mixture was cooled to ambient temperature, filtered and the filtrate was concentrated to a volume of 200 ml. The mixture was allowed to stand at ambient temperature for 16 hours. The precipitate was isolated to give the required starting material as a solid (15 g), m.p. 160–164° C.

NMR Spectrum (CDCl₃) 1.22 (s, 9H), 2.66 (s, 3H), 4.68 (s, 2H), 6.09 (s, 2H), 7.68 (s, 1H), 8.31 (s, 1H).

j) Elemental analysis showed that the product contained 1 equivalent of water and 0.5 equivalents of sodium chloride.

The pentafluorophenyl p-[N-(7-chloro-2-methyl-4-oxo-3-(pivaloyloxmethyl)-3,4-dihydroquinazolin-6-ylmethyl)-N-(prop-2-ynyl)amino]benzoate, used as a starting material, was obtained from 6-bromomethyl-7-chloro-2-methyl-3-(pivaloyloxyethyl)-3,4-dihydroquinazolin-4-one and tert-butyl p-(prop-2 -ynyl)aminobenzoate [prepared by the reaction of tert-butyl p-aminobenzoate with propargyl bromide] using analogous procedures to these described in the portion of Example 1 which is concerned with the preparation of starting materials.

k) Elemental analysis showed that the product contained 1 equivalent of water, 0.25 equivalents of diethyl ether and 1.5 equivalents of sodium chloride.

The pentafluorophenyl p-[N-(7-chloro-2-methyl-4-oxo-3-(pivaloyloxymethyl)-3,4-dihydroquinazolin-6-ylmethyl)-N-(prop-2-ynyl)amino]-o-fluorobenzoate, used as a starting material, was obtained from 6-bromomethyl-7-chloro-2-methyl-3-(pivaloyloxymethyl)-3,4-dihydroquinazolin-4-one and tert-butyl o-fluoro-p-(prop-2-ynyl)-aminobenzoate using analogous procedures to those described in the portion of Example 1 which is concerned with the preparation of starting materials.

l) Elemental analysis showed that the product contained 1.5 equivalents of water and 1 equivalent of sodium chloride.

The pentafluorophenyl p-[N-(7-bromo-2-methyl-4-oxo-3-(pivaloyloxymethyl)-3,4-dihydroquinazolin-6-ylmethyl)-N-methylamino]-o-fluorobenzoate, used as a starting material, was obtained from 7-bromo-6-bromomethyl-2-methyl-3-(pivaloyloxymethyl)-3,4-dihydroquinazolin-4-one (European Patent Application No. 0459730, Example 23 thereof) and tert-butyl o-fluoro-p-methylaminobenzoate using analogous procedures to those described in the portion of Example 1 which is concerned with the preparation of starting materials.

m) Elemental analysis showed that the product contained 1 equivalent of water and 0.6 equivalents of sodium chloride.

The product gave the following characteristic NMR signals: (CD₃SOCD₃) 2.2 (m, 2H), 2.34 (s, 3H), 2.95 (t, 2H), 3.2 (s, 1H), 4.4 (broad s, 3H), 4.7 (s, 2H), 6.79 (d, 2H), 7.72–7.8 (q, 4H), 8.46 (d, 1H), 12.28 (s, 1H).

The pentafluorophenyl p-[N-(7-bromo-2-methyl-4-oxo-3-(pivaloyloxymethyl)-3,4-dihydroquinazolin-6-ylmethyl)-N-methylamino]-o-fluorobenzoate, used a starting material, is described in European Patent Application No. 0459730, Example 23 thereof.

n) Elemental analysis showed that the product contained 2 equivalents of water and 3 equivalents of sodium chloride.

The pentafluorophenyl p-[N-(7-bromo-2-methyl-4-oxo-3-(pivaloyloxymethyl)-3,4-dihydroquinazolin-6-ylmethyl)-N-(prop-2-ynyl)amino]-o-fluorobenzoate, used as starting material, was obtained from 7-bromo-6-bromomethyl-2-methyl-3-(pivaloyloxymethyl)-3,4-dihydroquinazolin-4-one and tert-butyl o-fluoro-p-(prop-2-ynyl)aminobenzoate using analogous procedures to those described in the portion of Example 1 which is concerned with the preparation of starting materials.

EXAMPLE 3

Using analogous procedures to those described in Example 1, pentafluorophenyl o-fluoro-p-[N-(2,7-dimethyl-4-oxo-3-(pivaloyloxy-methyl)-3,4-dihydroquinazolin-6-ylmethyl)-N-(prop-2-ynyl)amino]benzoate was reacted with methyl (2S)-2-amino-4-(tetrazol-5-yl)butyrate and the methyl butyrate so obtained was hydrolysed to give (2S)-2-{o-fluoro-p-[N-(297-dimethyl-4-oxo-3,4-dihydroquinazolin-6-ylmethyl)-N-(prop-2-ynyl)amino]benzamido}-4-(tetrazol-5-yl)butyric acid (dried by azeotropic distillation of water from a toluene mixture) in 76% yield.

NMR Spectrum: (CD₃SOCD₃) 2.06–2.28 (m 3H), 2.97 (m, 2H), 3.21 (s, 1H), 4.30 (s, 2H), 4.42 (m, 1H), 4.70 (s, 2H), 6.65 (m, 2H), 7.43 (s, 1H), 7.59 (t, 1H), 7.71 (s, 1H), 8.05 (t, 1H), 12.06 (s, 1H); Mass Spectrum: (positive ion FAB) m/e (P+1) 533; Elemental Analysis: Found C, 57.8; H, 4.8; N, 20.3; $C_{26}H_{25}FN_8O_4$ 0.38H₂O 0.14Na⁺ 0.045Cl⁻ 0.04CH₃C₆H₅ requires C, 57.6; H, 4.8; N, 20.4%.

In this example, the methyl (2S)-2-amino-4-(tetrazol-5-yl)-butyrate was enriched in the form having the (S)-configuration to the extent that the ratio of (S):(R) form was 99:1 or greater as determined by chromatographic analysis. This isomeric ratio was retained in the product of Example 3.

The methyl (2S)-2-amino-4-(tetrazol-5-yl)butyrate (in which the ratio of (S):(R) form was 99:1 or greater) used as a starting material was obtained as follows:

A solution of N-benzyloxycarbonyl-L-glutamine methyl ester (25 g) in THF (500 ml) was added dropwise to a stirred solution of triphenylphosphine (44.5 g) in carbon tetrachloride (1L). The mixture was heated to 50° C. for 2 hours. The mixture was evaporated. The resultant oil was triturated in ethyl acetate. The mixture was filtered and the filtrate was evaporated. The residue was purified by column chromatography using a 1:1 mixture of hexane and ethyl acetate as eluent. There was thus obtained acetyl (2S)-2-benzyloxycarbonyl-amino-4-cyanobutyrate (19.38 g, 83%).

A mixture of methyl (2S)-2-benzyloxycarbonylamino-4-cyano-butyrate (10 g), tri-n-butyltin azide [prepared according to the method in *Rec. Trav. Chim. Pays-Bas*, 1963, 81, 286; 12 g] and THF (60 ml) was stirred and heated to reflux for 40 hours. The mixture was evaporated. The resultant brown oil was triturated in diethyl ether which had been saturated with hydrogen chloride gas. The precipitate was isolated and washed with diethyl ether. There was thus obtained methyl (2S)-2-benzyloxycarbonylamino-4-(tetrazol-5-yl)butyrate (2.23 g, 32%). MR Spectrum: ($CD_3SOCD_3$) 1.95–2.35 (m, 2H), 2.95 (t, 2H), 3.64 (s, 3H), 4.15 (m, 1H), 5.04 (s, 2H), 7.36 (s, 5H), 7.88 (d, 1H), 13.0 (s, 1H).

A mixture of the product so obtained was hydrogenated using an analogous procedure to that described in the last paragraph of Example 1. There was thus obtained methyl (2S)-2-amino-4-(tetrazol-5-yl)butyrate in 88% yield.

NMR Spectrum: ($CD_3SOCD_3$) 1.82–2.26 (m, 2H), 2.86–2.94 (t, 2H), 3.67 (s, 3H), 3.7–3.85 (m, 1H), 5.28 (broad s, 2H).

EXAMPLE 4

Diethylphosphoryl cyanide (0.18 g) was added to a mixture of 5-[N-(2,7-dimethyl-4-oxo-3,4-dihydroquinazolin-6-ylmethyl)-N-(prop-2-ynyl)amino]pyridine-2-carboxylic acid (0.135 g), N-methylmorpholine (0.113 g) and DMF (10 ml). The mixture was stirred at ambient temperature for 1 hour. A solution of a mixture of methyl (2S)-2-amino-4-(tetrazol-5-yl)butyrate (0.14 g) and N-methylmorpholine (0.113 g) in DMF (5 ml) was added. The resultant mixture was stirred at ambient temperature for 64 hours. The mixture was evaporated and the residue was partitioned between ethyl acetate and water. The organic phase was washed with water, dried (MgSO4) and evaporated. There was thus obtained methyl (2S)-2-{5-[N-(2,7-dimethyl-4-oxo-3,4-dihydroquinazolin-6-ylmethyl)-N-(prop-2-ynyl)amino]pyridine-2-carboxamido}-4-(tetrazol-5-yl)butyrate (0.16 g).

NMR Spectrum: ($CD_3SOCD_3$) 2.31 (m, 5H), 2.44 (s, 3H), 2.92 (t, 2H), 3.63 (s, 3H), 4.30 (s, 2H), 4.50 (m, 1H), 4.75 (s, 2H;), 7.20–7.31 (m, 1H), 7.44 (s, 1H), 7.72 (s, 1H), 7.80–7.90 (d, 1H), 8.13–8.20 (d, 1H), 8.65–8.77 (d, 1H), 12.1 (broad s, 1H).

A mixture of the material so obtained and 2N sodium hydroxide solution (3 ml) was stirred at ambient temperature for 1 hour. The mixture was acidified to pH4 by the addition of concentrated hydrochloric acid. The precipitate was isolated, washed in turn with water, acetone and diethyl ether and dried. There was thus obtained (2S)-2-{5-[N-(2,7-dimethyl-4-oxo-3,4-dihydroquinazolin-6-ylmethyl)-N-(prop-2-ynyl)amino]pyridine-2-carboxamido}-4-(tetrazol-5-yl)butyric acid (0.124 g).

NMR Spectrum: ($CD_3SOCD_3$) 2.30 (m, 5H), 2.45 (s, 3H), 2.82–2.89 (t, 2H), 4.39 (s, 2H), 4.42–4.60 (m, 1H), 4.76 (s, 2H), 7.2–7.31 (m, 1H), 7.45 (s, 1H), 7.73 (s, 1H), 7.8–7.9 (d, 1H), 8.15 (d, I;), 8.32–8.61 (d, 1H);

Mass Spectrum: (positive ion FAB) m/e (P+1) 515; Elemental Analysis: Found C, 48.0; H, 4.3; M, 19.8; $C_{25}H_{25}N_9O_4$ 1.5NaCl 1.25$H_2O$ requires C, 48.0; H, 4.4; M, 20.15%.

In this example, the methyl (2S)-2-amino-4-(tetrazol-5-yl)-butyrate was enriched in the form having the (S)-configuration to the extent that the ratio of (S):(R) form was 99:1 or greater as determined by chromatographic analysis. This isomeric ratio was retained in the product of Example 4.

The 5-[N-(2,7-dimethyl-4-oxo-3,4-dihydroquinazolin-6-ylmethyl)-N-prop-2-ynyl)amino]pyridine2-carboxylic acid used as a starting material was obtained as follows:

A mixture of 6-bromomethyl-2,7-dimethyl-3-(pivaloyloxymethyl)-3,4-dihydroquinazolin-4-one (1.11 g), methyl 5[N-(prop-2-ynyl)amino]pyridine-2-carboxylate 10.61 g; obtained in quantitative yield by treating methyl 5-[N-tert-butoxycarbonyl)-N-(prop-2-ynyl)-amino]pyridine-2-carboxylate (*J. Med. Chem.*, 1991, 1594) with trifluoroacetic acid at 0° C. for 1 hour], 2,6-lutidine (0.62 g), sodium iodide (0.005 g) and DMA (20 ml) gas stirred and heated to 95° C. for 7 hours. The mixture was evaporated and the residue was partitioned between ethyl acetate and a 2N hydrochloric acid solution. The acidity of the aqueous layer was reduced to $pH_4$ by the addition of 2N sodium hydroxide solution and the solution was extracted with ethyl acetate. The organic layer was dried ($MgSO_4$) and evaporated. The residue was purified by column chromatography using ethyl acetate as eluent. There was thus obtained methyl 5-[N-(2,7-dimethyl-4-oxo-3-(pivaloyloxymethyl)-3,4-dihydroquinazolin-6-ylmethyl)-N-(prop-2-ynyl)amino]-pyridine-2-carboxylate as a gum (0.262 g)

A mixture of the ester so obtained, 2N sodium hydroxide solution (20 ml) and methanol (10 ml) was stirred at ambient temperature for 16 hours. The bulk of the methanol was evaporated and the residual aqueous solution was acidified to pH6 by the addition of concentrated hydrochloric acid. The resultant precipitate was isolated, washed in turn with water and diethyl ether and dried. There was thus obtained 5-[N-(2,7-dimethyl-4-oxo-3,4-dihydroquinazolin-6-ylmethyl)-N-(prop-2-ynyl)amino]pyridine-2-carboxylic acid (0.143 g).

NMR Spectrum: ($CD_3SOCD_3$) 2.30 (s, 3H), 2.45 (s, 3H), 3.28 (s, 1H), 4.35 (s, 2H), 4.75 (s, 2H), 7.12–7.25 (m, 1H), 7.45 (s, 1H), 7.71 (s, 1H), 7.82–7.91 (d, 1H), 8.17–8.22 (d, 1H).

EXAMPLE 5

Using analogous procedures to those described in Example 1 pentafluorophenyl p-{N-[1-(2,7-dimethyl-4-oxo-3-(pivaloyloxymethyl)-3,4-dihydroquinazolin-6-yl)ethyl]-N-(prop-2-ynyl)amino}benzoate was reacted with methyl (2S)-2-amino-4-(tetrazol-5-yl)butyrate and the resultant methyl butyrate was hydrolysed to give 2- {p-{N-[1-(2,7-dimethyl-4-oxo-3,4-dihydroquinazolin-6-yl)ethyl]-N-(prop-2-ynyl)amino}benzamido}-4-(tetrazol-5-yl)butyric acid in 25% yields m.p. 207° C.

NMR Spectrum: ($CD_3SOCD_3$) 1.5 (d, 3H) 2.25 (m2 2H), 2.27 (s, 3H), 2.34 (s, 3H), 2.9 (s, 1H), 3.0 (t, 2H), 3.7 (d, 1H), 3.95 (d, 1H), 4.4 (m, 1H), 5.5 (m, 1H), 7.0 (d, 2H), 7.4 (s, 1H), 7.8 (d, 2H), 8.1 (s, 1H) 8.4 (d, 1H); Elemental Analysis: Found C, 57.9; H, 5.2; N, 19.5; $C_{27}H_{28}N_8O_4$ $1H_2O$ 0.25NaCl requires C, 57.7; H, 5.3; N, 19.9%.

In this example the methyl (2S)-2-amino-4-(tetrazol-5-yl)-butyrate was enriched in the form having the (S)-configuration to the extent that the ratio of (S):(R) was 7:3. This isomeric ratio was retained in the product of Example 5.

The pentafluorophenyl p-{N-1-(2,7-dimethyl-4-oxo-3-(pivaloyloxymethyl)-3,4-dihydroquinazolin-6-yl)ethyl-N-(prop-2-ynyl)-amino}benzoate used as a starting material was obtained as follows:

Bromine (9.4 g) was added dropwise to a stirred solution of 4'-ethyl-3'-methylacetanilide in acetic acid (100 ml) which had been warmed to 45° C. The mixture was stirred at 45° C. for 30 minutes. The mixture was evaporated and the residue was partitioned between ethyl acetate and a saturated aqueous sodium bicarbonate solution. The organic phase was washed with water, dried ($MgSO_4$) and evaporated. The residue was purified by column chromatography using a 5:1 v/v mixture of hexane and ethyl acetate as eluent. There was thus obtained 2'-bromo-4'-ethyl-5'-methylacetanilide (13.2 g), m.p. 92° C.

A mixture of the compound so obtained, cuprous cyanide (6.8 g) and NMP (100 ml) was stirred and heated to 120° C. for 1 hour. The mixture was cooled to ambient temperature, poured onto a mixture of aqueous ammonium hydroxide (0.88 g/ml, 300 ml) and ice (600 ml) and stirred for 10 minutes. The precipitate was isolated and washed in turn with water and with ethyl acetate. The organic washings were washed with water and with brine, dried ($MgSO_4$) and evaporated. There was thus obtained 2'-cyano-4'-ethyl-5l-methylacetanilide (8 g), m.p. 121° C.

A mixture of the material so obtained, hydrogen peroxide (30%, 150 ml), sodium hydroxide (2.33 g) and water (23 ml) was stirred and heated to 55° C. for 2 hours. The mixture was cooled to ambient temperature and the mixture gas evaporated. Eater (200 ml) was added to the residue and the solution was acidified to $pH_4$ by the addition of dilute aqueous hydrochloric acid. The precipitate was isolated, washed with water and dried. There was thus obtained 6-ethyl-2,7-dimethyl-3,4-dihydroquinazolin-4-one (6.7 g), m.p. 288° C. (decomposes).

NMR Spectrum ($CD_3SOCD_3$) 1.2 (t, 3H), 2.3 (s, 3H), 2.35 (s, 3H), 2.7 (q, 2H), 7.3 (s, 1H), 7.8 (s, 1H), 11.95 (broad s, 1H).

A solution of the material so obtained in DMSO (50 ml) was added to a stirred mixture of sodium hydride (80% dispersion in mineral oil, 1.5 g; from which the oil had been washed by hexane) and DMSO (50 ml). The mixture was stirred at ambient temperature for 30 minutes. Chloromethyl pivalate (9.7 g) was added and the mixture was stirred at ambient temperature for 20 hours. The mixture was partitioned between ethyl acetate and a mixture of ice and water. The organic phase was washed with water, dried ($MgSO_4$) and evaporated. The product was purified by column chromatography using increasingly polar mixtures of hexane and ethyl acetate as eluent. There was thus obtained 6-ethyl-2,7-dimethyl-3-(pivaloyloxymethyl)-3,4-dihydroquinazolin-4-one (4.2 g), m.p. 104° C.

A mixture of a portion (3.2 g) of the product so obtained, N-bromosuccinimide (1.9 g), benzoyl peroxide (0.01 g) and carbon tetrachloride (300 ml) was stirred and heated to reflux for 3 hours. The mixture was cooled to ambient temperature and filtered. The filtrate was evaporated and the residue was purified by column chromatography using increasingly polar mixtures of hexane and ethyl acetate as eluent. There was thus obtained 6-(1-bromoethyl)-2,7-dimethyl-3-(pivaloyloxymethyl)-3,4-dihydroquinazolin-4-one (3.35 g) m.p. 132° C.

NMR Spectrum ($CDCl_3$) 1.25 (s, 9H), 2.2 (d, 3H), 2.55 (s, 3H), 2.65 (s, 3H), 3.4 (q, 1H), 6.1 (q, 2H), 7.43 (s, 1H), 8.4 (s, 1H).

A mixture of the product so obtained, tert-butyl p-aminobenzoate (4.8 g), calcium carbonate (3.3 g) and DMA (80 ml) was stirred and heated to 110° C. for 3 hours. The mixture was evaporated and the residue was partitioned between ethyl acetate and water. The organic phase was dried ($MgSO_4$) mad evaporated. The residue was purified by column chromatography using increasingly polar mixtures of hexane and ethyl acetate as eluent. There was thus obtained tert-butyl p-{N-[1-(2,7-dimethyl-4-oxo-3-(pivaloyloxymethyl)-3,4-dihydroquinazolin-6-yl)ethyl]amino}benzoate (2.75 g) m.p. 220° C.

A mixture of a portion (1.5 g) of the material so obtained, propargyl bromide (80% solution in toluene, 3.3 ml), calcium carbonate (1.5 g) and DMA (50 ml) was stirred and heated to 110° C. for 8 hours. The mixture was evaporated and the residue was partitioned between ethyl acetate and water. The organic phase was dried ($MgSO_4$) and evaporated. The residue was purified by column chromatography using a 1:1 v/v mixture of hexane and ethyl acetate as eluent. There was thus obtained tert-butyl p-{N-[1-(2,7-dimethyl-4-oxo-3-(pivaloyloxymethyl)-3,4-dihydroquinazolin-6-yl)ethyl]-N-(prop-2-ynyl)amino}benzoate as a gum (0.78 g).

NMR Spectrum ($CDCl_3$) 1.23 (s, 9H), 1.57 (s, 9H), 1.72 (d, 3H), 2.0 (t, 1H, 2.3 (s, 3H), 2.63 (s, 3H), 3.7 (m, 1H), 3.9 (m, 1H), 5.3 (q, 1H), 6.1 (s, 2H), 6.95 (d, 2H), 7.42 (m, 1H), 7.95 (d, 2H), 8.3 (s, 1H).

A mixture of the product so obtained and trifluoroacetic acid (20 ml) was stirred at ambient temperature for 1 hour. The mixture was evaporated. Diethyl ether (100 ml) was added and the precipitate was isolated. There was thus obtained p-{N-[1-(2,7-dimethyl-4-oxo-3-(pivaloyloxymethyl)-3,4-dihydroquinazolin-6-yl)ethyl]-N-(prop-2-ynyl)-amino}benzoic acid trifluoroacetic acid salt (0.73 g) m.p. 217° C.

A mixture of the product so obtained, pentafluorophenol (0.64 g), dicyclohexylcarbonate (0.717 g) and ethyl acetate (120 ml) was stirred at ambient temperature for 20 hours. The mixture was filtered and the filtrate was evaporated. The residue was purified by column chromatography using a 3:1 v/v mixture of hexane and ethyl acetate as eluent. There was thus obtained pentafluorophenyl p-{N-[1-(2,7-dimethyl-4-oxo-3-(pivaloyloxymethyl)-3,4-dihydroquinazolin-6-yl)ethyl]-N-(prop-2-ynyl)amino}benzoate (0.68 g), m.p. 112° C.

EXAMPLE 6

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |

-continued

| | | |
|---|---|---|
| Maize starch paste (5% w/v paste) | 2.25 | |
| Magnesium stearate | 3.0 | |
| (b) Tablet II | | mg/tablet |
| Compound X | 50 | |
| Lactose Ph.Eur | 223.75 | |
| Croscarmellose sodium | 6.0 | |
| Maize starch | 15.0 | |
| Polyvinylpyrrolidone (5% w/v paste) | 2.25 | |
| Magnesium stearate | 3.0 | |
| (c) Tablet III | | mg/tablet |
| Compound X | 1.0 | |
| Lactose Ph.Eur | 93.25 | |
| Croscarmellose sodium | 4.0 | |
| Maize starch paste (5% w/v paste) | 0.75 | |
| Magnesium stearate | 1.0 | |
| (d) Capsule | | mg/capsule |
| Compound X | 10 mg | |
| Lactose Ph.Eur | 488.5 | |
| Magnesium stearate | 1.5 | |
| (e) Injection I | | (50 mg/ml) |
| Compound X | 5.0% w/v | |
| 1 M Sodium hydroxide solution | 15.0% v/v | |
| 0.1 M Hydrochloric acid (to adjust pH to 7.6) | | |
| Polyethylene glycol 400 | 4.5% w/v | |
| Water for injection to 100% | | |
| (f) Injection II | | (10 mg/ml) |
| Compound X | 1.0% w/v | |
| Sodium phosphate BP | 3.6% w/v | |
| 0.1 M Sodium hydroxide solution | 15.0% v/v | |
| Water for injection to 100% | | |
| (g) Injection III | | (1 mg/ml, buffered to pH 6) |
| Compound X | 0.1% w/v | |
| Sodium phosphate BP | 2.26% w/v | |
| Citric acid | 0.38% w/v | |
| Polyethylene glycol 400 | 3.5% w/v | |
| Water for injection to 100% | | |

The above formulations may be obtained by conventional procedures well known in the pharmaceutical art. The tablets (a) to (c) may be enteric coated by conventional means, for example to provide a coating of cellulose acetate phthalate.

CHEMICAL FORMULAE

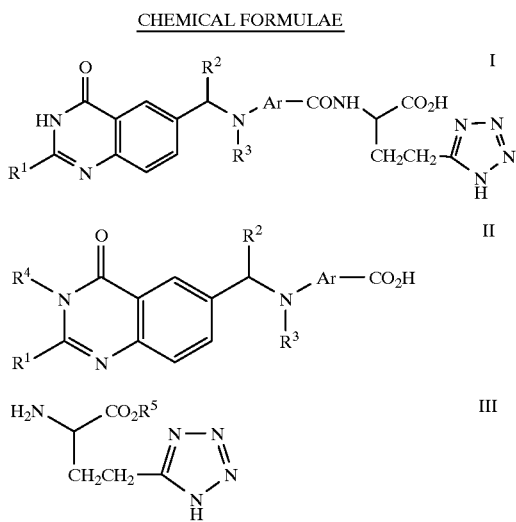

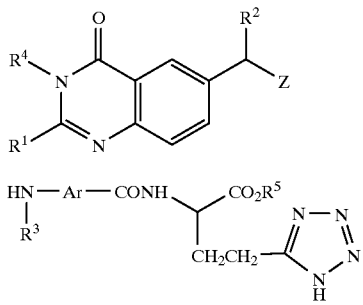

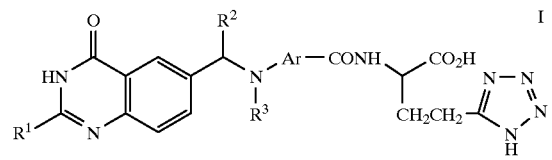

What we claim is:

1. A quinazoline derivative of the formula I wherein $R^1$ is (1–4C)alkyl;

the quinazoline ring may optionally bear (at one or two of the 5-, 7- and 8-positions) one or two further substituents selected from halogeno, (1–4C)alkyl and (1–4C)alkoxy;

$R^2$ is hydrogen or (1–4C)alkyl;

$R^3$ is hydrogen, (1–4C)alkyl, (3–4C)alkenyl, (3–4C)alkynyl, hydroxy-(2–4C)alkyl, halogeno-(2–4C)alkyl or cyano-(1–4C)alkyl;

and Ar is phenylene or heterocyclene which may optionally bear one or two substituents selected from halogeno, (1–4C)alkyl and (1–4C)alkoxy;

or a pharmaceutically-acceptable salt or ester thereof.

2. A quinazoline derivative of the formula I as claimed in claim 1 wherein $R^1$ is methyl;

the quinazoline ring may optionally bear a 7-fluoro, 7-chloro, 7-bromo or 7-methyl substituent;

$R^2$ is hydrogen;

$R^3$ is methyl, ethyl, propyl, prop-2-enyl or prop-2-ynyl; and

Ar is 1,4-phenylene which may optionally bear one fluoro substituent, or Ar is thiophene-2,5-diyl, thiazole-2,5-diyl (with the —CONH— group in the 2-position) or pyridine-2,5-diyl (with the —CONH— group in the 2-position);

or a pharmaceutically-acceptable salt thereof.

3. A quinazoline derivative of the formula I as claimed in claim 1 wherein $R^1$ is methyl;

the quinazoline ring may optionally bear a 7-fluoro, 7-chloro, 7-bromo or 7-methyl substituent;

$R^2$ is hydrogen;

$R^3$ is methyl, ethyl or prop-2-ynyl; and

Ar is 1,4-phenylene, 2-fluoro-1,4-phenylene (with the —CONH— group in the 1-position), or pyridine-2,5-diyl (with the —CONH— group in the 2-position);

or a pharmaceutically-acceptable salt thereof.

4. A quinazoline derivative of the formula I as claimed in claim 1 wherein $R^1$ is methyl;

the quinazoline ring bears a 7-methyl substituent;

$R^2$ is hydrogen;

$R^3$ is methyl, ethyl or prop-2-ynyl; and

Ar is 1,4-phenylene or 2-fluoro-1,4-phenylene (with the —CONH— group in the 1-position);

or a pharmaceutically-acceptable salt thereof.

5. A quinazoline derivative of the formula I as claimed in claim 1 wherein $R^1$ is methyl;

the quinazoline ring bears a 7-methyl substituent;

$R^2$ is hydrogen;

$R^3$ is methyl or prop-2-ynyl; and

Ar is 1,4-phenylene, 2-fluoro-1,4-phenylene (with the —CONH— group in the 1-position), or pyridine-2,5-diyl (with the —CONH— group in the 2-position);

or a pharmaceutically-acceptable salt thereof.

6. A quinazoline derivative of the formula I as claimed in claim 1, or a pharmaceutically-acceptable salt thereof, selected from the group consisting of:

2-{p-[N-(2-methyl-4-oxo-3,4-dihydroquinazolin-6-ylmethyl)-N-(prop-2-ynyl)amino]benzamido}-4-(tetrazol-5-yl)butyric acid, 2-{o-fluoro-p-[N(2-methyl-4-oxo-3,4-dihydroquinazolin-6-ylmethyl)-N-(prop-2-ynyl)amino]benzamido}-4-(tetrazol-5-yl)butyric acid, 2-{p-[N-(2,7-dimethyl-4-oxo-3,4-dihydroquinazolin-6-ylmethyl)-N-methylamino]benzamido}-4-(tetrazol-5-yl)butyric acid, 2-{o-fluoro-p-[N-(2,7-dimethyl-4-oxo-3,4-dihydroquinazolin-6-ylmethyl)-N-methylamino]benzamido}-4-(tetrazol-5-yl)butyric acid, 2-{p-[N-(2,7-dimethyl-4-oxo-3,4-dihydroquinazolin-6-ylmethyl)-N-(prop-2-ynyl)amino]benzamido}-4-(tetrazol-5-yl)butyric acid, 2-{o-fluoro-p-[N-(2,7-dimethyl-4-oxo-3,4-dihydroquinazolin-6-ylmethyl)-N-(prop-2-ynyl)amino]benzamido}-4-(tetrazol-5-yl)butyric acid, 2-{p-[N-(7-chloro-2-methyl-4-oxo-3,4-dihydroquinazolin-6-ylmethyl)-N-(prop-2-ynyl)amino]benzamido}-4-(tetrazol-5-yl)butyric acid, 2-{o-fluoro-p-[N-(7-chloro-2-methyl-4-oxo-3,4-dihydroquinazolin-6-ylmethyl)-N-(prop-2-ynyl)amino]benzamido}-4-(tetrazol-5-yl)butyric acid and 2-{p-[N-(7-bromo-2-methyl-4-oxo-3,4-dihydroquinazolin-6-ylmethyl)-N-(prop-2-ynyl)amino]benzamido}-4-(tetrazol-5-yl)butyric acid.

7. A quinazoline derivative of the formula I as claimed in claim 1, or a pharmaceutically-acceptable salt thereof, selected from the group consisting of:

(2S)-2-{p-[N-(2-methyl-4-oxo-3,4-dihydroquinazolin-6-ylmethyl)-N-(prop-2-ynyl)amino]benzamido}-4-(tetrazol-5-yl)butyric acid, (2S)-2-{o-fluoro-p-[N-(2-methyl-4-oxo-3,4-dihydroquinazolin-6-ylmethyl)-N-(prop-2-ynyl)amino]benzamido}-4-(tetrazol-5-yl)butyric acid, (2S)-2-{p-[N-(2,7-dimethyl-4-oxo-3,4-dihydroquinazolin-6-ylmethyl)-N-methylamino]benzamido}-4-(tetrazol-5-yl)butyric acid, (2S)-2-{o-fluoro-p-[N-(2,7-dimethyl-4-oxo-3,4-dihydroquinazolin-6-ylmethyl)-N-methylamino]benzamido}-4-(tetrazol-5-yl)butyric acid, (2S)-2-{p-[N-(2,7-dimethyl-4-oxo-3,4-dihydroquinazolin-6-ylmethyl)-N-ylmethyl)-N-(prop-2-ynyl)amino]benzamido}-4-(tetrazol-5-yl)butyric acid, (2S-2-{o-fluoro-p-[N-(2,7-dimethyl-4-oxo-3,4-dihydroquinazolin-6-ylmethyl)-N-(prop-2-ynyl)amino]benzamido}-4-(tetrazol-5-yl)butyric acid, (2S)-2-{o-[N-(7-chloro-2-methyl-4-oxo-3,4-dihydroquinazolin-6-ylmethyl)-N-prop-2-ynyl)amino]benzamido}-4-(tetrazol-5-yl)butyric acid, (2S)-2-{o-fluoro-p-[N-(7-chloro-2-methyl-4-oxo-3,4-dihydroquinazolin-6-ylmethyl)-N-(prop-2-ynyl)amino]benzamido}-4-(tetrazol-5-yl)butyric acid and (2S)-2-{p-[N-(7-bromo-2-methyl-4-oxo-3,4-dihydroquinazolin-6-ylmethyl)-N-(prop-2-ynyl)amino]benzamido}-4-(tetrazol-5-yl)butyric acid.

8. A quinazoline derivative of the formula I as claimed in claim 1, or a pharmaceutically-acceptable salt thereof, selected from the group consisting of:

(2S)-2-{o-fluoro-p-[N-(2,7-dimethyl-4-oxo-3,4-dihydroquinazolin-6-ylmethyl)-N-(prop-2-ynyl)amino]benzamido}-4-(tetrazol-5-yl)butyric acid and (2S)-2-{5-[N-(2,7-dimethyl-4-oxo-3,4-dihydroquinazolin-6-ylmethyl)-N-(prop-2-ynyl)amino]pyridine-2-carboxamido}-4-(tetrazol-5-yl)butyric acid.

9. A quinazoline derivative of the formula I as claimed in claim 1, or a pharmaceutically-acceptable salt thereof, being:

(2S)-2-{o-fluoro-p-[N-(2,7-dimethyl4-oxo-3,4-dihydroquinazolin-6-ylmethyl)-N-(prop-2-ynyl)amino]benzamido}4-(tetrazol-5-yl)butyric acid.

10. A pharmaceutical composition which comprises a quinazoline derivative of the formula I, or a pharmaceutically-acceptable salt or ester thereof, as claimed in any one of claims 1, 3, 7 and 9 in association with a pharmaceutically-acceptable diluent or carrier.

11. A method for producing an anti-tumour effect in a warm-blooded animal in need of such treatment which comprises administering to said animal an effective amount of a quinazoline derivative of the formula I, or a pharmaceutically-acceptable salt or ester thereof, as claimed in any one of claims 1, 3, 7 and 9.

12. A method for producing an anti-tumour effect in a warm-blooded animal having a thymidylate synthase sensitive tumour selected from leukaemia and breast, lung, colon, rectal, stomach, prostate, bladder, pancreatic and ovarian cancer, which comprises administering to said animal an effective amount of a quinazoline of the formula I, or a pharmaceutically-acceptable salt thereof, as defined in any one of claims 1, 3, 7 and 9.

13. A method for producing an anti-proliferative effect in a warm-blooded animal in need of such treatment which comprises administering to said animal an effective amount of a quinazoline derivative of the formula I, or a pharmaceutically-acceptable salt thereof, as defined in any one of claims 1, 3, 7 and 9.

14. A method for producing an anti-proliferative effect mediated alone or in part by inhibition of the enzyme thymidylate synthase in a warm-blooded animal which comprises administering to said animal an effective amount of a quinazoline derivative of the formula I, or a pharmaceutically-acceptable salt thereof, as defined in any one of claims 1, 3, 7 and 9.

15. A method for treating the proliferation of malignant cells in a warm-blooded animal characterised by inhibition of the enzyme thymidylate synthase by administration to said animal of an effective amount of a quinazoline derivative of the formula I, or a pharmaceutically-acceptable salt thereof, as defined in any one of claims 1, 3, 7 and 9.

16. A method for producing a thymidylate synthase inhibitory effect in a warm-blooded animal in need of such treatment which comprises administering to said animal an effective amount of a quinazoline derivative of the formula I, or a pharmaceutically-acceptable salt thereof, as defined in any one of claims 1, 3, 7 and 9.

17. A method for treating in a warm-blooded animal a disease or medical condition mediated alone or in part by the enzyme thymidylate synthase which comprises administering to said animal an effective amount of a quinazoline derivative of the formula I, or a pharmaceutically-acceptable salt thereof, as defined in any one of claims 1, 3, 7 and 9.

* * * * *